United States Patent
Chung et al.

(10) Patent No.: US 11,152,082 B2
(45) Date of Patent: Oct. 19, 2021

(54) PROTEIN MEMORY CELL AND PROTEIN MEMORY SYSTEM

(71) Applicants: Hongik University Industry-Academia Cooperation Foundation, Seoul (KR); Myongji University Industry and Academia Cooperation Foundation, Yongin-si (KR)

(72) Inventors: Minsub Chung, Seoul (KR); Sangmin Lee, Seoul (KR); Hwajin Lee, Seoul (KR); Tran Nguyen Anh Nhung, Seoul (KR); Dohyun Kim, Seoul (KR); Nebiyu Getachew Arega, Yongin-si (KR); Minh Khang Chau, Yongin-si (KR)

(73) Assignees: HONGIK UNIVERSITY INDUSTRY-ACADEMIA COOPERATION FOUNDATION, Seoul (KR); MYONGJI UNIVERSITY INDUSTRY AND ACADEMIA COOPERATION FOUNDATION, Yongin-si (KR)

( * ) Notice: Subject to any disclaimer, the term of this patent is extended or adjusted under 35 U.S.C. 154(b) by 94 days.

(21) Appl. No.: 16/799,389

(22) Filed: Feb. 24, 2020

(65) Prior Publication Data

US 2021/0225459 A1 Jul. 22, 2021

(30) Foreign Application Priority Data

Jan. 16, 2020 (KR) .................. 10-2020-0006084

(51) Int. Cl.
*G16B 50/30* (2019.01)
*B01L 3/00* (2006.01)
(Continued)

(52) U.S. Cl.
CPC .......... *G16B 50/30* (2019.02); *B01L 3/50273* (2013.01); *C07K 14/43504* (2013.01); *G01N 27/44795* (2013.01); *B01L 2300/02* (2013.01)

(58) Field of Classification Search
CPC . G16B 50/30; B01L 3/50273; B01L 2300/02; C07K 14/43504; G01N 27/44795
See application file for complete search history.

(56) References Cited

U.S. PATENT DOCUMENTS 8,709,892 B2   4/2014   Mao et al.
8,883,719 B2   11/2014  Birge et al.
(Continued)

FOREIGN PATENT DOCUMENTS

KR   100928561   11/2009
KR   101627832   6/2016

*Primary Examiner* — Jennifer Wecker
(74) *Attorney, Agent, or Firm* — Cantor Colburn LLP

(57) ABSTRACT

A protein memory cell and a protein memory system are provided. The protein memory cell includes: first and second electrodes disposed to be spaced apart from each other on a micro channel; a gap region defined between the first and second electrodes on the micro channel; an outer region defined as an opposite side to the gap region based on the first or second electrode on the micro channel; and a photosensitive protein changing conductivity between the first and second electrodes while moving between the gap region and the outer region depending on structural conversion of a chromophore.

20 Claims, 6 Drawing Sheets

Specification includes a Sequence Listing.

(51) Int. Cl.
*G01N 27/447* (2006.01)
*C07K 14/435* (2006.01)

(56) References Cited

U.S. PATENT DOCUMENTS

| | | |
|---|---|---|
| 9,208,864 B2 | 12/2015 | Sethi |
| 2004/0115614 A1* | 6/2004 | Burnett .................. C12Q 1/025 435/4 |
| 2008/0191265 A1 | 8/2008 | Mao et al. |
| 2009/0268511 A1 | 10/2009 | Birge et al. |
| 2013/0294180 A1 | 11/2013 | Litsyn et al. |
| 2015/0103591 A1 | 4/2015 | Sethi |

\* cited by examiner

SEQUENCE LISTING

<160> NUMBER OF SEQ ID NOS: 7

<210> SEQ ID NO 1
<211> LENGTH: 238
<212> TYPE: PRT

<213> ORGANISM: Artificial Sequence
<220> FEATURE:
<223> OTHER INFORMATION: Synthetic_wtGFP(wild-type Green Fluorescent Protein)

<400> SEQUENCE: 1

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235
```

<210> SEQ ID NO 2
<211> LENGTH: 34
<212> TYPE: DNA
<213> ORGANISM: Artificial Sequence
<220> FEATURE:
<223> OTHER INFORMATION: Synthetic_F64L forward primer

<400> SEQUENCE: 2
cactactctc tcttatggtg ttcaatgctt ttca        34

<210> SEQ ID NO 3
<211> LENGTH: 29
<212> TYPE: DNA
<213> ORGANISM: Artificial Sequence
<220> FEATURE:
<223> OTHER INFORMATION: Synthetic_F64L reverse primer

<400> SEQUENCE: 3
taagagagag tagtgacaag tgttggcca        29

<210> SEQ ID NO 4
<211> LENGTH: 27

```
<212> TYPE: DNA
<213> ORGANISM: Artificial Sequence
<220> FEATURE:
<223> OTHER INFORMATION: Synthetic_F64V forward primer

<400> SEQUENCE: 4
cttgtcacta ctgtctctta tggtgtt                                       27

<210> SEQ ID NO 5
<211> LENGTH: 27
<212> TYPE: DNA
<213> ORGANISM: Artificial Sequence
<220> FEATURE:
<223> OTHER INFORMATION: Synthetic_F64V reverse primer

<400> SEQUENCE: 5
aacaccataa gagacagtag tgacaag                                       27

<210> SEQ ID NO 6
<211> LENGTH: 27
<212> TYPE: DNA
<213> ORGANISM: Artificial Sequence
<220> FEATURE:
<223> OTHER INFORMATION: Synthetic_F64I forward primer

<400> SEQUENCE: 6
cttgtcacta ctatctctta tggtgtt                                       27

<210> SEQ ID NO 7
<211> LENGTH: 27
<212> TYPE: DNA
<213> ORGANISM: Artificial Sequence
<220> FEATURE:
<223> OTHER INFORMATION: Synthetic_F64I reverse primer

<400> SEQUENCE: 7
aacaccataa gagatagtag tgacaag                                       27
```

PROTEIN MEMORY CELL AND PROTEIN MEMORY SYSTEM

CROSS-REFERENCE TO RELATED APPLICATION

This application claims priority to and the benefit of Korean Patent Application No. 10-2020-0006084 filed in the Korean Intellectual Property Office on Jan. 16, 2020, the entire contents of which are incorporated herein by reference.

BACKGROUND

(a) Technical Field

The present disclosure relates to a protein memory cell and a protein memory system.

(b) Description of the Related Art

Bioelectronics simultaneously having advantages of a semiconductor device and advantages of biogenic materials has been spotlighted as a technology capable of being complementary to existing silicon based semiconductors due to a rapid information transmission rate, high energy efficiency, possibility of large-scale integration, low heat generation, possibility of parallel information processing, and biocompatibility. As a protein based memory technology is a bioelectronic technology capable of exhibiting a logical value depending on changes of protein state, various studies on the protein based memory technology have been conducted. In this regard, a method for improving performance and stability of a writing/reading operation of the protein based memory has been demanded.

The above information disclosed in this Background section is only for enhancement of understanding of the background of the disclosure and therefore it may contain information that does not form the prior art that is already known in this country to a person of ordinary skill in the art.

SUMMARY

The present disclosure has been made in an effort to provide a protein memory cell and a protein memory system having advantages of improving to performance and stability of a writing/reading operation.

An example embodiment of the present disclosure provides a protein memory cell including: first and second electrodes disposed to be spaced apart from each other on a micro channel; a gap region defined between the first and second electrodes on the micro channel; an outer region defined as an opposite side to the gap region based on the first or second electrode on the micro channel; and a photosensitive protein changing conductivity between the first and second electrodes while moving between the gap region and the outer region depending on structural conversion of a chromophore.

When a structure of the chromophore is converted from a first structure into a second structure, the photosensitive protein may move from the outer region to the gap region.

When the structure of the chromophore is converted from the first structure into the second structure, the conductivity between the first and second electrodes may be decreased.

When the structure of the chromophore is converted from the first structure into the second structure, a logical value of the protein memory cell may be changed from a first logical value to a second logical value.

When a structure of the chromophore is converted from a second structure into a first structure, the photosensitive protein may move from the gap region to the outer region.

When the structure of the chromophore is converted from the second structure into the first structure, the conductivity between the first and second electrodes may be increased.

When the structure of the chromophore is converted from the second structure into the first structure, a logical value of the protein memory cell may be changed from a second logical value to a first logical value.

The photosensitive protein may include one or more of green fluorescent protein (GFP) mutants having an amino acid sequence in which phenylalanine positioned adjacent to an N-terminal of an amino acid sequence (SYG) of the chromophore is substituted with one of leucine, isoleucine, and valine in an amino acid sequence of wild-type green fluorescent protein (wtGFP from *Aequorea victoria*).

Another embodiment of the present disclosure provides a protein memory cell including: first and second electrodes disposed to be spaced apart from each other on a micro channel; a gap region defined between the first and second electrodes on the micro channel; an outer region defined as an opposite side to the gap region based on the first or second electrode on the micro channel; and green fluorescent protein (GFP) having an amino acid sequence in which phenylalanine positioned adjacent to an N-terminal of an amino acid sequence (SYG) of a chromophore is substituted with one of leucine, isoleucine, and valine in an amino acid sequence of wild-type green fluorescent protein (wtGFP), wherein the GFP moves between the first and second electrodes depending on light irradiated from a light source.

When first light is irradiated from the light source, the GFP may move from the outer region to the gap region.

When the first light is irradiated from the light source, conductivity between the first and second electrodes may be decreased.

When the first light is irradiated from the light source, a logical value of the protein memory cell may be changed from a first logical value to a second logical value.

When second light is irradiated from the light source, the GFP may move from the gap region to the outer region.

When the second light is irradiated from the light source, conductivity between the first and second electrodes may be increased.

When the second light is irradiated from the light source, the logical value of the protein memory cell may be changed from a second logical value to a first logical value.

Yet another embodiment of the present disclosure provides a protein memory system including: a protein memory cell including first and second electrodes disposed to be spaced apart from each other on a micro channel, a gap region defined between the first and second electrodes on the micro channel, an outer region defined as an opposite side to the gap region based on the first or second electrode on the micro channel, and green fluorescent protein (GFP) having an amino acid sequence in which phenylalanine positioned adjacent to an N-terminal of an amino acid sequence (SYG) of a chromophore is substituted with one of leucine, isoleucine, and valine in an amino acid sequence of wild-type green fluorescent protein (wtGFP); a light source performing a writing operation on the protein memory cell; and a readout circuit electrically connected to the first and second electrodes to perform a reading operation for the protein memory cell.

The light source may irradiate first light to the protein memory cell to record a second logical value in the protein memory cell.

The light source may irradiate second light to the protein memory cell to record a first logical value in the protein memory cell.

The readout circuit may determine a state in which the GFP is positioned in the gap region with a second logical value.

The readout circuit may determine a state in which the GFP is positioned in the outer region with a first logical value.

According to an embodiment of the present disclosure, since a conversion rate between on and off states of the photosensitive protein is significantly high (about 99%), a signal-to-noise ratio for data readout of the protein memory cell may be significantly improved, and thus performance and stability of the writing/reading operation of the protein memory cell may also be significantly improved.

DETAILED DESCRIPTION

Example embodiments of the present disclosure will be described in detail with reference to the accompanying drawings so that those skilled in the art to which the present disclosure pertains may easily practice the present disclosure.

As those skilled in the art would realize, the described embodiments may be modified in various different ways, all without departing from the spirit or scope of the present disclosure. Portions unrelated to the description will be omitted in the drawings in order to obviously describe the present disclosure, and the same or similar components will be denoted by the same reference numerals throughout the present specification. In addition, a detailed description for a well-known technology will be omitted.

Throughout the present specification, unless explicitly described to the contrary, the word "comprise" and variations such as "comprises" or "comprising", will be understood to imply the inclusion of stated elements but not the exclusion of any other elements.

In the present specification, for convenience of explanation, the case in which a protein memory cell and a protein memory system are mainly implemented as a non-volatile memory cell and a non-volatile memory system is described, but the scope of the present disclosure is not limited thereto. Therefore, it will be understood that the protein memory cell and the protein memory system may be realized as a volatile memory cell and a volatile memory system according to specific implementation purpose.

Figure 1:
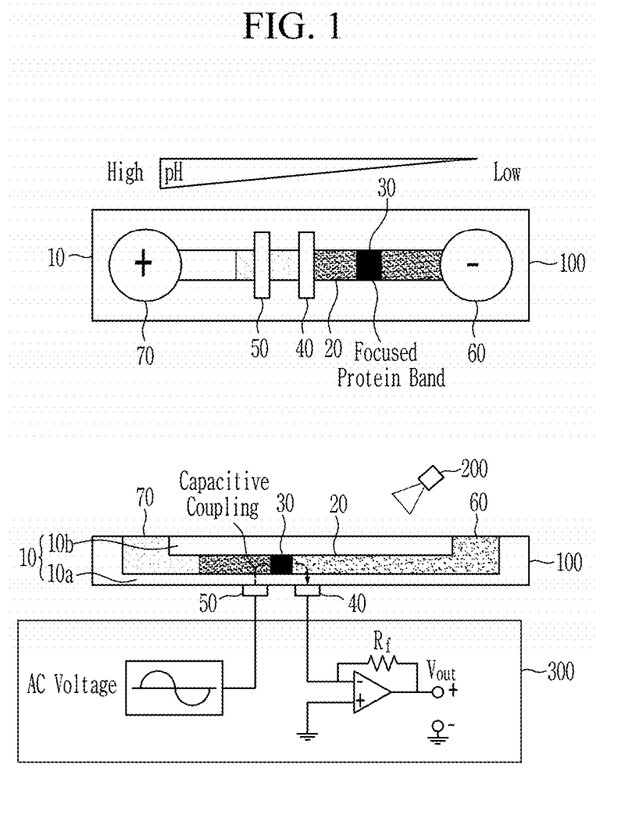
FIG. 1 is a view for explaining a protein memory system according to an example embodiment of the present disclosure.

FIG. 1 is a view for explaining a protein memory system according to an example embodiment of the present disclosure.

Referring to FIG. 1, the protein memory system according to the example embodiment of the present disclosure may include a protein memory cell 100, a light source 200, and a readout circuit 300.

The protein memory cell 100 may include a substrate 10, a micro channel 20, a photosensitive protein 30, and electrodes 40 and 50.

Any material may be used as the substrate 10 as long as it has physical properties suitable for forming the micro channel 20. However, in order to use a non-volatile protein memory system as a memory system for recording biochemical information later, it is preferable that the substrate 10 is made of a biocompatible material. Further, in order to appropriately transmit light irradiated from the light source 200 for writing and erasing data to the protein memory cell 100, the substrate 100 may also be made of a light transmittable material.

In the present example embodiment, the substrate 10 may be made of cyclic olefin co-polymer (COC), polydimethylsiloxane (PDMS), polymethyl methacrylate (PMMA), polycarbonate (PC), or the like, but the scope of the present disclosure is not limited thereto.

The micro channel 20 may contain the photosensitive protein 30. In detail, the micro channel 20 may contain the photosensitive protein 30 so as to be movable.

In the present example embodiment, the photosensitive protein 30 may be positioned in an initial state, that is, an initial digital state (for example, a logic low (L) state) using an isoelectric focusing (IEF) method.

As the IEF method, a carrier ampholyte (CA)-IEF method may be used, or an immobilized pH-gradient (IPG)-IEF method in which a polyacrylamide gel is copolymerized and immobilized with a pH-gradient may be applied.

In addition, the photosensitive protein 30 may also be positioned in the initial digital state by additionally performing a focusing step of separating the photosensitive protein 30 to an isoelectric point and a mobilization step of moving the focused protein to an analysis place. In this case, as a mobilization method, a chemical mobilization method, an electro-osmotic flow mobilization method, a pressure difference mobilization method, or the like, may be used.

The electrodes 40 and 50 may be disposed to be spaced apart from each other on the micro channel 20. Since a surface 10a on which the electrodes 40 and 50 are formed is capacitively coupled between the electrodes 40 and 50, the surface 10a may be formed to have a thickness of several hundreds µm or less, preferably, 100 µm or less. Meanwhile, the surface 10a on which the electrodes 40 and 50 are formed may be made of biocompatible and transparent plastic such as COC, PDMS, PMMA, PC, or the like.

A gap region and an outer region may be defined on the micro channel 20. The gap region may be defined between first and second electrodes 50 and 40 on the micro channel 20. For example, in FIG. 1, the gap region may be defined as the right side of the first electrode 50 and the left side of the second electrode 40.

In addition, the outer region may be defined as an opposite side to the gap region based on the first or second electrode 50 or 40 on the micro channel 20. For example, in FIG. 1, the outer region may be defined as the left side of the first electrode 50 or the right side of the second electrode 40.

The photosensitive protein 30 may record information in the protein memory cell 100 or read recorded information using a photoswitching property. For example, light irradiated from the light source 200 may become an input signal of the light memory cell 100, and an accompanying change in an electrical state, that is, a change in isoelectric point of the photosensitive protein 30 may express information. Therefore, in order to improve performance and stability of the protein memory cell 100, there is a need to adopt a protein in which a change in electrical state, that is, change of the isoelectric point of the photosensitive protein 30 is clearly shown.

The photosensitive protein 30 may be a green fluorescent protein (GFP). The GFP is a protein utilized as marker in biological studies, and a wild-type green fluorescent protein (wtGFP from *Aequorea victoria*), which is one of the most widely used GFPs, may have the following amino acid sequence.

(SEQ ID No: 1)
MSKGEELFTGWPILVELDGDVNGHKFSVSGEGEGDATYGKLTLKFIC

TTGKLPVPWPTLVTTF<u>SYG</u>VQCFSRYPDHMKQHDFFKSAMPEGYVQERTI

FFKDDGNYKTRAEVKFEGDTLVNRIELKGIDFKEDGNILGHKLEYNYNSH

NVYIMADKQKNGIKVNFKIRHNIEDGSVQLADHYQQNTPIGDGPVLLPDN

HYLSTQSALSKDPNEKRDHMVLLEFVTAAGITHGMDELYK

The green fluorescent protein (GFP) mentioned as the photosensitive protein in the present specification may include a mutant of which a function as the marker (for example, photosensitivity) is improved as well as the wtGFP including the amino acid sequence of SEQ ID No: 1.

In the example embodiment, the GFP mutant capable of being used as the photosensitive protein 30 may include a GFP (GFP-F64L) having an amino acid sequence in which phenylalanine (F) positioned in front of an amino acid sequence (SYG) of a chromophore indicated by an underline in the amino acid sequence (SEQ ID No: 1) of the wtGFP, that is, phenylalanine positioned adjacent to an N-terminal of the amino acid sequence (SYG) of the chromophore is substituted with leucine (L). In another example embodiment, a GFP mutant capable of being used as the photosensitive protein 30 may include one or more GFPs having an amino acid sequence in which phenylalanine (F) positioned adjacent to an N-terminal of the amino acid sequence (SYG) of the chromophore, indicated by an underline, in the amino acid sequence (SEQ ID No: 1) of the wtGFP, is substituted with one of isoleucine (I) and valine (V). In the description relating to the amino acid sequence of the protein in the present specification, it may be interpreted that the terms "having", "comprising", "consisting essentially of", "consisting of", and "represented by" are compatibly used in an equivalent sense for the purpose of specifying the amino acid sequence constituting proteins and do not preclude the case in which mutations such as addition, substitution, deletion, and/or the like, of some of amino acids that do not induce a significant functional and/or structural change of the protein in the amino acid sequence of the protein are introduced.

In the case in which the GFP-F64L is adopted as the photosensitive protein 30, operation performance and stability of the protein memory cell 100 may be significantly improved. For example, the photosensitive protein 30 of GFP-F64L may be converted into an off state by irradiating UV light having a wavelength in a range of 340 to 390 nm, and it is possible to measure through a fluorescence microscope that a conversion rate thereof is 99%, which is significantly high as compared to wtGFP. In the case of the GFP having an amino acid sequence in which phenylalanine (F) is substituted with one of isoleucine (I) and valine (V), high operation performance and stability similar to the GFP-F64L may be exhibited.

The light source 200 may irradiate light for performing a writing operation, a reading operation, and an erasing operation of the data to the protein memory cell 100. To this end, the light source 200 may be implemented using a device having light with a specific wavelength such as a light emitting diode (LED) or an optical filter.

The light source 200 may irradiate light having a predetermined wavelength, for example, UV light, blue light, or the like. In detail, the light source 200 may irradiate first light (for example, UV light) to the protein memory cell 100 to record a second logical value, for example, logic low (L) in the protein memory cell 100. Further, the light source 200 may irradiate second light (for example, blue light) to the protein memory cell 100 to record a first logical value, for example, logic high (H) in the protein memory cell 100.

As described above, the light source 200 may irradiate light of UV light-blue light combination in order to implement a writing operation, a reading operation, and the like, of data, the scope of the present disclosure is not limited thereto. That is, various combinations such as green light-red light combination, UV light-green light combination, and the like, may also be used.

Meanwhile, in consideration of body implantable application, the light irradiated from the light source 200 may be skin transmittable light.

The readout circuit 300 may be electrically connected to the electrodes 40 and 50 to perform a reading operation for the protein memory cell 100.

As the readout circuit 300, any circuit capable of reading information in an optical, electrical, or mass method may be used as long as it is a circuit capable of reading information stored in the protein memory cell 100 based on a position change or position state of the photosensitive protein 30. Among them, as the electrical method, a voltage method, a current method, a conductivity method, a non-contact conductivity method, or the like, may be applied. In the case of applying the non-contact conductivity method, since there is no need to insert an electrode in a channel, a process may be simplified, and side effects such as electrolysis, and the like, may be significantly decreased, such that a circuit using the non-contact conductivity method may be considered as a preferable readout circuit. Since a high frequency is used, the readout circuit may be implemented in a non-contact manner, and the non-contact conductivity method may be accomplished with coupling electrodes 40 and 50 and an impedance measuring circuit. Since the impedance measuring circuit may be implemented by a complementary metal-oxide semiconductor (CMOS) integration circuit technology, it may be easy to down-size and implement the impedance measuring circuit. However, the scope of the present disclosure is not limited thereto, but a readout circuit 300 using various impedance measuring methods capable of implementing the non-contact conductivity method may be applied.

Figure 2:
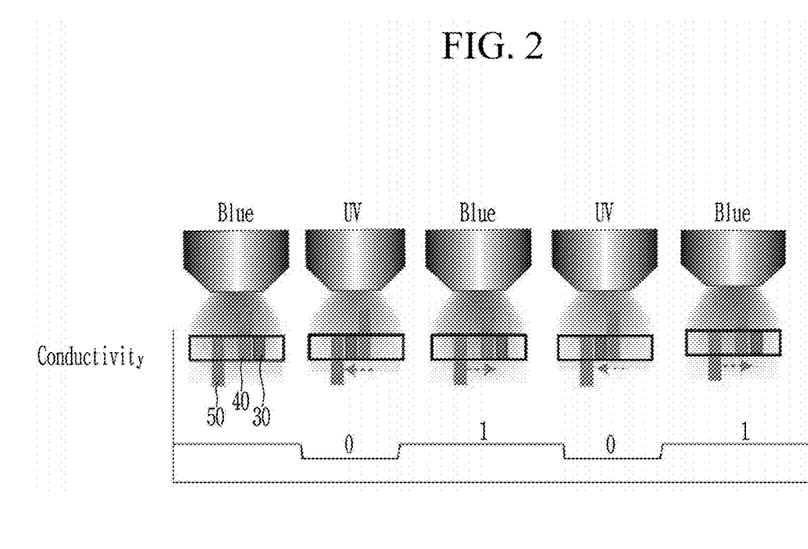
FIGS. 2 to 4 are views for explaining a protein memory cell according to an example embodiment of the present disclosure.
Figure 3:
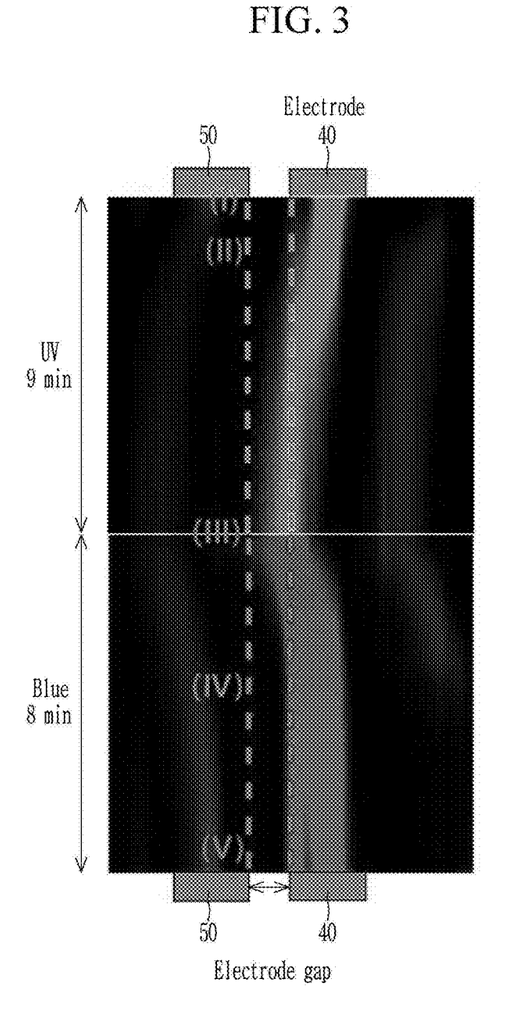
Figure 4:
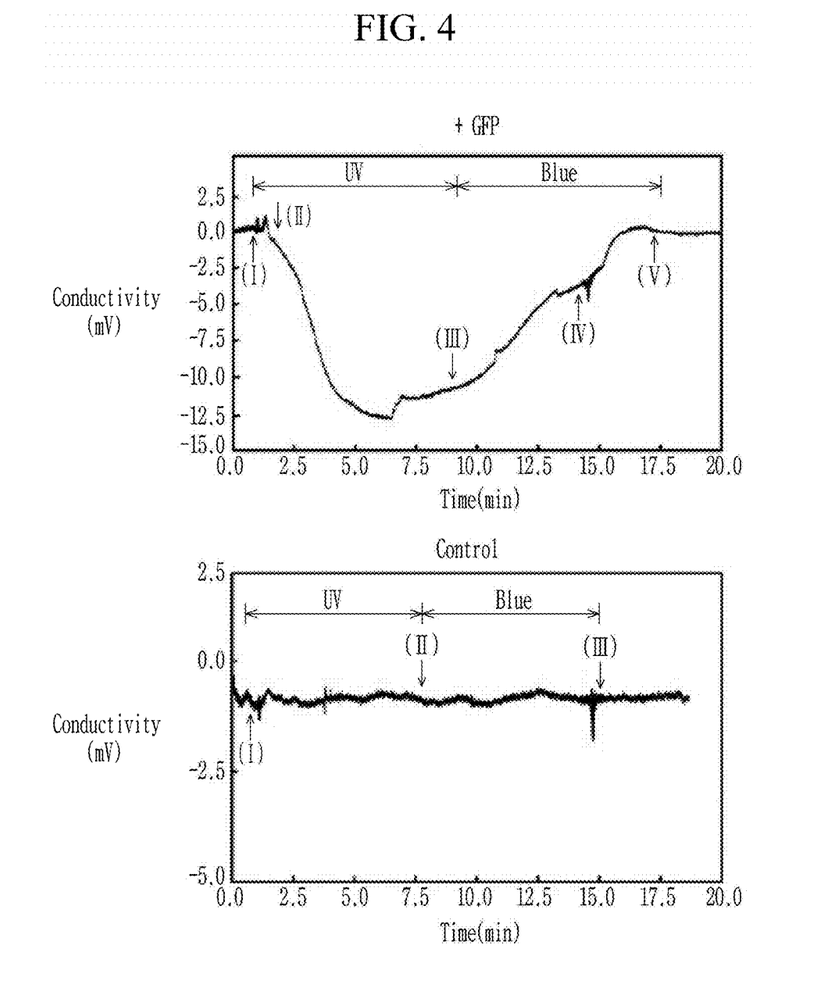

FIGS. 2 to 4 are views for explaining a protein memory cell according to an example embodiment of the present disclosure.

Referring to FIG. 2, the case in which the protein memory cell 100 generates light-switching of the photosensitive protein 30 using UV light and blue light irradiated from the light source 200 as input signals to record information is shown.

The photosensitive protein 30 may move between the first and second electrodes 50 and 40 depending on the light irradiated from the light source 200.

Specifically, when the first light (for example, UV light) is irradiated from the light source 200, the photosensitive protein 30 may move from the outer region to the gap region. In this case, conductivity between the first and second electrodes 50 and 40 may be decreased, and a logical value of the protein memory cell 100 may be changed from the first logical value (H or 1) to the second logical value (L or 0).

Unlike this, when the second light (for example, blue light) is irradiated from the light source 200, the photosensitive protein 30 may move from the gap region to the outer region. In this case, conductivity between the first and second electrodes 50 and 40 may be increased, and the logical value of the protein memory cell 100 may be changed from the second logical value (L or 0) to the first logical value (H or 1).

Then, referring to FIGS. 3 and 4, in the case in which the first light (for example, UV light) is irradiated to the protein memory cell 100 for about 9 minutes, the photosensitive protein 30 located toward the second electrode 40 outside the gap region gradually moves to the gap region. Thereafter, in the case in which the second light (for example, blue light) is irradiated to the protein memory cell 100 for about 8 minutes, the photosensitive protein 30 located in the gap region gradually moves to the outer region toward the second electrode 40.

A graph shown in an upper portion of FIG. 4 shows conductivity changed with the passage of time in the case in which the first light (for example, UV light) and the second light (for example, blue light) are irradiated to the protein memory cell 100, and a graph shown in a lower portion of FIG. 4 is a graph illustrating a control group.

As shown in FIGS. 3 and 4, it may be appreciated that while the first light (for example, UV light) is irradiated to the protein memory cell 100 at the point (I) for about 9 minutes, there is no significant change in conductivity up to the (II) point, but conductivity is significantly decreased in a section from the point (II) to the point (III). The reason is that a rate at which the photosensitive protein 30, for example, GFP-F64L is converted from an on state into an off state during irradiation with UV light reaches about 99%.

In addition, it may be appreciated that in a section from the point (III) to the point (V) through the point (IV), conductivity is significantly increased again to approach a value similar to that at the point (I). The reason is that a rate at which the photosensitive protein 30 of GFP-F64L is converted from the off state into the on state during irradiation with the blue light also reaches about 99%.

According to the example embodiment, since the conversion rate of the photosensitive protein 30 between the on state and the off state is about 99%, which is significantly high, a signal-to-noise ratio of the protein memory cell 100 for data readout may be significantly improved, and thus, performance and stability of writing/reading operations of the protein memory cell 100 may also be significantly improved.

Figure 5:
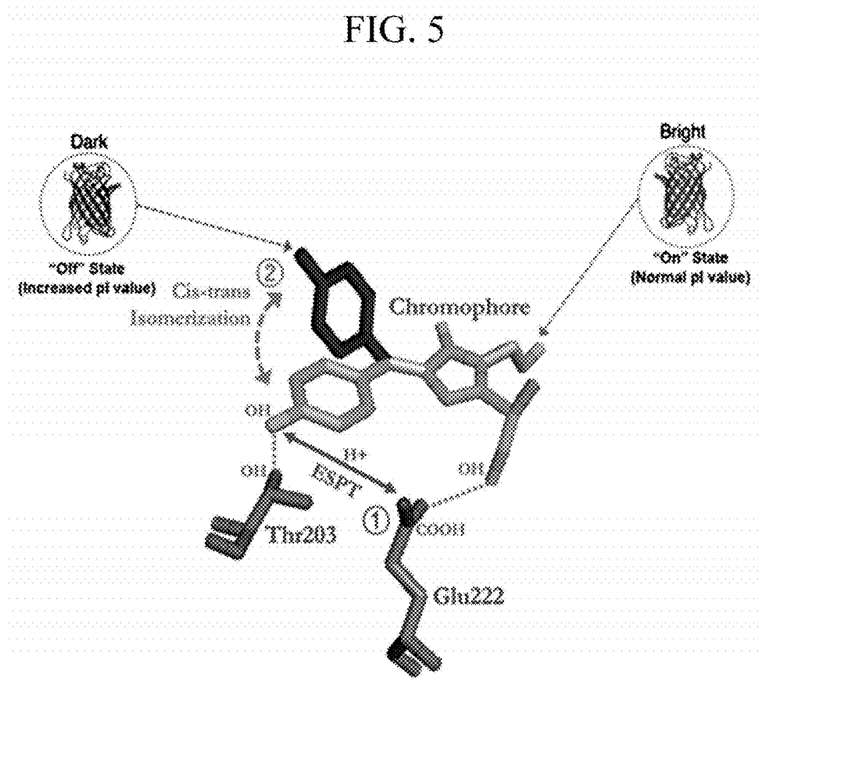
FIG. 5 is a view for explaining a photosensitive protein according to an example embodiment of the present disclosure.

FIG. 5 is a view for explaining the photosensitive protein according to the example embodiment of the present disclosure.

Referring to FIG. 5, the photosensitive protein 30 according to the example embodiment of the present disclosure has a high photoconversion efficiency. The photoconversion mechanism may be various, and as an example, the photoconversion may be a structural conversion of the chromophore of the photosensitive protein 30, that is, cis-trans conversion.

Cis-trans isomerization may occur due to protonation of the chromophore. Chromophores of most fluorescent proteins, including photosensitive protein 30 according to the example embodiment of the present disclosure, have a form in which two rings are linked by double bonds. In the on state (bright isoform), the chromophore may have a cis steric structure in which two rings are present in one plane and thus the chromophore exhibits the lowest energy, and in the off state (dark isoform), the chromophore may have a trans steric structure. In the case of irradiating the GFP with UV light, energy of the chromophore is increased, such that a cis form is converted into a trans form.

As a result of analyzing which residue structurally interacts with F64 first, it may be appreciated that the 46th residue phenylalanine and a benzene ring are adjacent up and down. This causes pi-pi stacking. Here, the term "pi-pi stacking" means that HOMO and LUMO pi orbitals overlap each other to be stabilized through hypercongugation. Due to this action, strong attraction may be generated between two residues, and thus the stabilized residues may be immobilized. However, strong attraction disappears simultaneously with substitution with leucine, and a structural change may occur in this portion. Thus, as a result of isoelectric photo-switching of a F64L mutant, a ratio of the off state (dark isoform) was significantly increased as compared to wtGFP.

When the on state is converted into the off state, the chromophore is isomerized from a cis structure to a trans structure. In this case, rotation of a hexagonal ring Y66 of the chromophore occurs, and as attraction between F64 linked to a pentagonal ring and F46 disappears, the force fixing the pentagonal ring of the chromophore may be decreased, such that two rings of the chromophore may relatively freely rotate. Therefore, it may be said that an effect of lowering energy barrier required for conversion from a protonated cis form into a deprotonated trans form is obtained. An effect of this structural change may contribute to a high conversion rate of 99%.

Referring to FIGS. 2 to 4 again, the photosensitive protein 30 may change conductivity between the first and second electrodes 50 and 40 while moving between the gap region and the outer region depending on conversion of the structure of the chromophore.

In detail, when the structure of the chromophore is converted from a first structure (cis structure) into a second structure (trans structure), the photosensitive protein may move from the outer region to the gap region. In this case, conductivity between the first and second electrodes 50 and 40 may be decreased, and the logical value of the protein memory cell may be changed to from the first logical value (H) to the second logical value (L).

Meanwhile, when the structure of the chromophore is converted from the second structure (trans structure) into the first structure (cis structure), the photosensitive protein may move from the gap region to the outer region. In this case, when the structure of the chromophore is converted from the second structure (trans structure) into the first structure (cis structure), conductivity between the first and second electrodes 50 and 40 may be increased, and when the structure of the chromophore is converted from the second structure (trans structure) into the first structure (cis structure), the logical value of the protein memory cell may be changed from the second logical value (L) to the first logical value (H).

Figure 6:
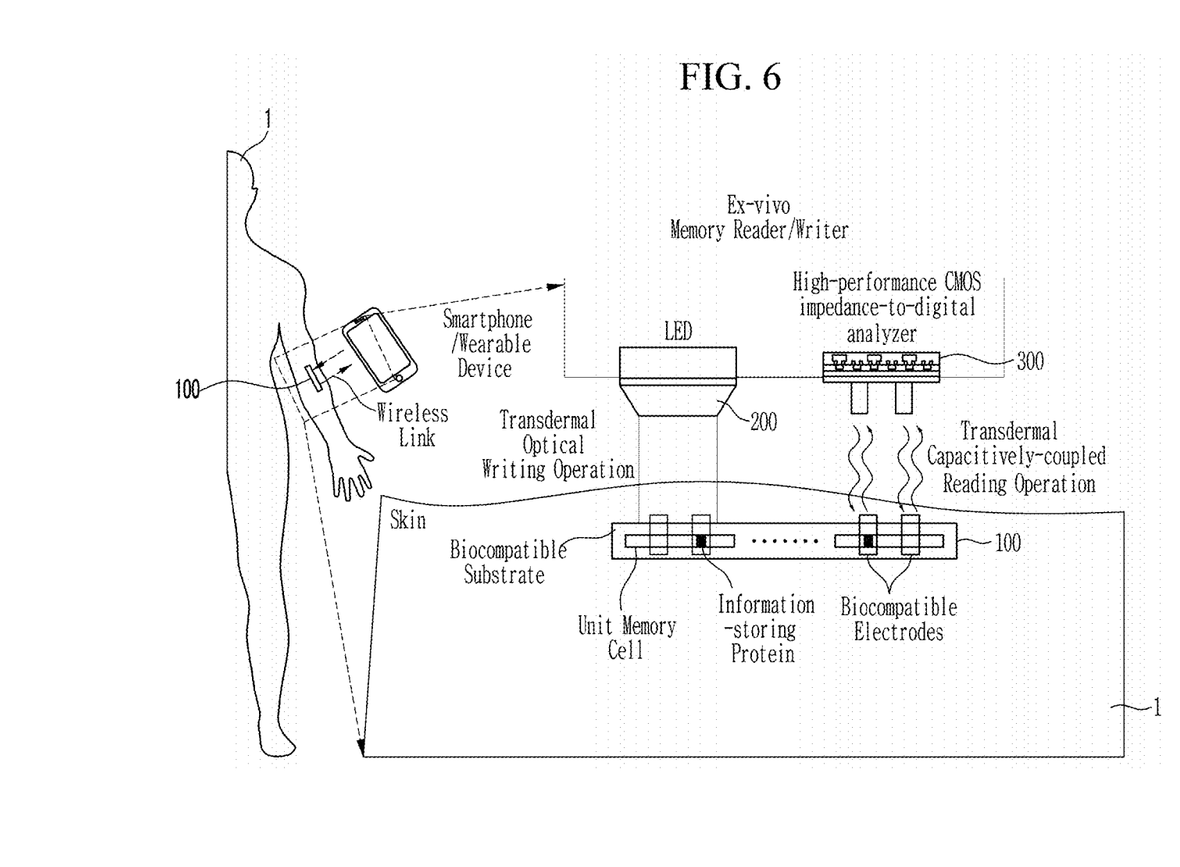
FIG. 6 is a view for explaining an example of applying the protein memory system according to the example embodiment of the present disclosure to a living body.

FIG. 6 is a view for explaining an example of applying the protein memory system according to the example embodiment of the present disclosure to a living body.

As shown in FIG. 6, the protein memory cell 100 may be installed in the living body and the light source 200 and the readout circuit 300 may be installed outside the living body to thereby be implemented as a body implantable ID card, a body implantable credit card, or the like.

EXPERIMENTAL EXAMPLE

1. Mutagenesis

Site directed mutagenesis was performed on a plasmid (pET-15b, clontech, USA) cloned with a gene fragment encoding His-tag linked GFP (SEQ ID No: 1) by a polymerase chain reaction (PCR) using Pfu DNA polymerase (Bioneer, Daejeon, Korea), and a resultant was treated with Dpn I (Takara, Shiga, Japan).

The PCR was performed as follows: pre-denaturation (94° C., 5 min), denaturation (94° C., 1 min), annealing (primer Tm, 1 min), and extension (72° C., 1 min/Kb) were performed. 20 to 25 cycles of denaturation, annealing, and extension were performed. Finally, after performing final extension (72° C., 5 min), the resultant was stored at 4° C.

A primer sequence used in PCR was as follows:
Used Primer Sequence

```
F64L forward
                                        (SEQ ID No: 2)
CACTACTCTCTCTTATGGTGTTCAATGCTTTTCA Tm 66.5° C.

F64L reverse
                                        (SEQ ID No: 3)
TAAGAGAGAGTAGTGACAAGTGTTGGCCA Tm 66.8° C.

F64V forward
                                        (SEQ ID No: 4)
CTTGTCACTACTGTCTCTTATGGTGTT Tm 65.3° C.

F64V reverse
                                        (SEQ ID No: 5)
AACACCATAAGAGACAGTAGTGACAAG Tm 65.3° C.

F64I forward
                                        (SEQ ID No: 6)
CTTGTCACTACTATCTCTTATGGTGTT Tm 63.7° C.

F64I reverse
                                        (SEQ ID No: 7)
AACACCATAAGAGATAGTAGTGACAAG Tm 63.7° C.
```

Thereafter, the obtained plasmid including the mutagenesis-induced GFP gene fragment was transformed into *Escherichia coli* BL21 (DE3) by heat shock. The *E. coli* transformed as described above were spreaded on a Luria-Bertani (LB) agar plate containing ampicillin (antibiotics) and incubated at 37° C. overnight (for 16 to 20 hours). Subsequently, after each colony is inoculated and cultured in 5 ml LB broth containing ampicillin, only plasmid DNA was extracted through plasmid preparation kit (Bioneer, Daejeon, Korea), followed by DNA sequence analysis. As a result, it was confirmed that F64L mutation (codon mutation: TTC→CTC), F64I mutation (codon mutation: TTC→ATC), or F64V mutation (codon mutation: TTC→GTC) was induced in the GFP encoded by the DNA.

2. Preparation of Protein

*E. coli* in which DNA encoding wild-type GFP (SEQ ID NO: 1) was introduced and *E. coli* in which DNA encoding the GFP mutant prepared in Example 1 were cultured in 15 mL LB medium containing ampicillin overnight (for 16 to 20 hours) and scaled up to 400 mL medium under the same conditions, respectively. When OD600 reached 0.4 to 0.6, a temperature of a shaking incubator was cooled to 22° C., followed by expression for 20 hours. The GFP was purified using a column filled with HF nickel affinity gel (Sigma) having affinity to His-tag linked to GFP and expressed together with GFP. In order to separate His-tag from GFP after purification using the nickel column, GFP was treated with thrombin (GE Healthcare) and purified by anion exchange using a Hitrap Q HP column (GE Healthcare) and fast protein liquid chromatography (FPLC, GE Healthcare, Buckinghamshire, U.K.) under an environment of 25 mM Tris/150 mM NaCl buffer (pH 7.4). The protein purified as described above was exchanged into 25 mM Tris buffer (pH 7.4) by ultrafiltration using Vivaspin (GE Healthcare, Buckinghamshire, U.K.).

3. Observation of Photoconversion Property Using Isoelectric Focusing (IEF)

A gel buffer was loaded on a micro channel and then allowed to stand for 10 minutes to thereby be coated on the entire channel. Thereafter, a loading buffer containing GFP was injected into a left hole and inverted into a right hole for 1 minute. Wells prepared in a form of a pipette tip were inserted into both holes of the channel, loading buffer was put into a left well, and the GFP-free gel buffer was put into a right well.

Electrodes were put into both wells, and while a voltage of 150 V was applied thereto and stabilized for 3 minutes, the channel was allowed to stand until a current reached to 15 uA or less. The buffer in the left well was exchanged with a 2× cathode buffer (10× cathode buffer: novex LC5310, 200 mM lysine, 200 mM arginine, pH 10.1), and the buffer in the right well was exchanged with a 20× anode buffer (bio-rad 161-0761, 140 mM H3PO4). Thereafter, a voltage of 150 V was applied thereto from left to right. It was observed that the current was decreased and stabilized simultaneously with focusing of GFP in the channel.

When the focusing was carried out, an illumination light of a microscope through a UV filter was irradiated to GFP in the channel for 2~9 min depending on switching distance. After switched to a blue filter, a change in isoelectric point was observed with a time-lapse of 1 second. The obtained results were shown in FIG. 3.

While this disclosure has been described in connection with what is to presently considered to be practical example embodiments, it is to be understood that the disclosure is not limited to the disclosed embodiments. On the contrary, it is intended to cover various modifications and equivalent arrangements included within the spirit and scope of the appended claims.

What is claimed is:

1. A protein memory cell comprising:
   first and second electrodes disposed to be spaced apart from each other on a micro channel;
   a gap region defined between the first and second electrodes on the micro channel;
   an outer region defined as an opposite side to the gap region based on the first or second electrode on the micro channel; and
   a photosensitive protein changing conductivity between the first and second electrodes while moving between the gap region and the outer region depending on structural conversion of a chromophore.

2. The protein memory cell of claim 1, wherein:
   when a structure of the chromophore is converted from a first structure into a second structure, the photosensitive protein moves from the outer region to the gap region.

3. The protein memory cell of claim 2, wherein:
   when the structure of the chromophore is converted from the first structure into the second structure, the conductivity between the first and second electrodes is decreased.

4. The protein memory cell of claim 2, wherein:
   when the structure of the chromophore is converted from the first structure into the second structure, a logical value of the protein memory cell is changed from a first logical value to a second logical value.

5. The protein memory cell of claim 1, wherein:
   when a structure of the chromophore is converted from a second structure into a first structure, the photosensitive protein moves from the gap region to the outer region.

6. The protein memory cell of claim 5, wherein:
   when the structure of the chromophore is converted from the second structure into the first structure, the conductivity between the first and second electrodes is increased.

7. The protein memory cell of claim 5, wherein:
   when the structure of the chromophore is converted from the second structure into the first structure, a logical value of the protein memory cell is changed from a second logical value to a first logical value.

8. The protein memory cell of claim 1, wherein:
   the photosensitive protein
   includes green fluorescent protein (GFP) having an amino acid sequence in which phenylalanine positioned adjacent to an N-terminal of an amino acid sequence (SYG) of the chromophore is substituted with one of leucine, isoleucine, and valine in an amino acid sequence of wild-type green fluorescent protein (wtGFP).

9. A protein memory cell comprising:
   first and second electrodes disposed to be spaced apart from each other on a micro channel;
   a gap region defined between the first and second electrodes on the micro channel;

an outer region defined as an opposite side to the gap region based on the first or second electrode on the micro channel; and green fluorescent protein (GFP) having an amino acid sequence in which phenylalanine positioned adjacent to an N-terminal of an amino acid sequence (SYG) of a chromophore is substituted with one of leucine, isoleucine, and valine in an amino acid sequence of wild-type green fluorescent protein (wtGFP), wherein the GFP moves between the first and second electrodes depending on light irradiated from a light source.

10. The protein memory cell of claim 9, wherein:
when first light is irradiated from the light source, the GFP moves from the outer region to the gap region.

11. The protein memory cell of claim 10, wherein:
when the first light is irradiated from the light source, conductivity between the first and second electrodes is decreased.

12. The protein memory cell of claim 10, wherein:
when the first light is irradiated from the light source, a logical value of the protein memory cell is changed from a first logical value to a second logical value.

13. The protein memory cell of claim 9, wherein:
when the second light is irradiated from the light source, the GFP moves from the gap region to the outer region.

14. The protein memory cell of claim 13, wherein:
when the second light is irradiated from the light source, conductivity between the first and second electrodes is increased.

15. The protein memory cell of claim 13, wherein:
when the second light is irradiated from the light source, a logical value of the protein memory cell is changed from a second logical value to a first logical value.

16. A protein memory system comprising:
a protein memory cell including first and second electrodes disposed to be spaced apart from each other on a micro channel,
a gap region defined between the first and second electrodes on the micro channel,
an outer region defined as an opposite side to the gap region based on the first or second electrode on the micro channel, and
green fluorescent protein (GFP) having an amino acid sequence in which phenylalanine positioned adjacent to an N-terminal of an amino acid sequence (SYG) of a chromophore is substituted with one of leucine, isoleucine, and valine in an amino acid sequence of wild-type green fluorescent protein (wtGFP);
a light source performing a writing operation on the protein memory cell; and
a readout circuit electrically connected to the first and second electrodes to perform a reading operation for the protein memory cell.

17. The protein memory system of claim 16, wherein:
the light source irradiates first light to the protein memory cell to record a second logical value in the protein memory cell.

18. The protein memory system of claim 16, wherein:
the light source irradiates second light to the protein memory cell to record a first logical value in the protein memory cell.

19. The protein memory system of claim 16, wherein:
the readout circuit determines a state in which the GFP is positioned in the gap region with a second logical value.

20. The protein memory system of claim 16, wherein:
the readout circuit determines a state in which the GFP is positioned in the outer region with a first logical value.

* * * * *